(12) United States Patent
Kavadi

(10) Patent No.: US 10,265,548 B1
(45) Date of Patent: Apr. 23, 2019

(54) SEGMENTED ULTRASOUND BODY SUIT

(71) Applicant: Raj Kavadi, Sugar Land, TX (US)

(72) Inventor: Raj Kavadi, Sugar Land, TX (US)

( * ) Notice: Subject to any disclaimer, the term of this patent is extended or adjusted under 35 U.S.C. 154(b) by 370 days.

(21) Appl. No.: 14/728,571

(22) Filed: Jun. 2, 2015

(51) Int. Cl.
*A61H 1/00* (2006.01)
*A61N 7/00* (2006.01)
*A41D 13/12* (2006.01)

(52) U.S. Cl.
CPC .......... *A61N 7/00* (2013.01); *A41D 13/1263* (2013.01); *A61N 2007/0004* (2013.01); *A61N 2007/0078* (2013.01)

(58) Field of Classification Search
CPC .............................. A61N 7/00; A61H 23/0245
See application file for complete search history.

(56) References Cited

U.S. PATENT DOCUMENTS

| 7,758,490 B2 | 7/2010 | Pilla et al. |
| 8,340,740 B2 | 12/2012 | Holzer et al. |
| 8,465,433 B2 | 6/2013 | Zwirn |
| 2008/0086072 A1* | 4/2008 | Bonutti ..................... A61F 7/00 604/21 |
| 2016/0317383 A1* | 11/2016 | Stanfield ................ A61N 1/323 |

\* cited by examiner

*Primary Examiner* — Hien Nguyen

(57) ABSTRACT

A segmented ultrasound body suit having a suit assembly with a plurality of separated segments having a torso and buttocks segment, a pair of mirror image arm segments, a pair of mirror image thigh segments, and a pair of mirror image calf segments. A plurality of cutouts is disposed in the segments. Each cutout is affixed within with a pad containing a power source and a switched ultrasound transducer and pressure switch. An ultrasound energy is transferred to a skin contact surface by a plate housed within the pad. A user dons any or all segments for chosen ultrasound treatment, with choice of off and on at each pad.

16 Claims, 5 Drawing Sheets

SEGMENTED ULTRASOUND BODY SUIT

BACKGROUND OF THE INVENTION

If the various types of ultrasound devices known to treat human ailments, a few offer a sleeve or the like to address a particular body part, such as a forearm for example. What has been needed is a substantially full body suit than provides a plurality of ultrasound treatment pads that address a plurality of major body areas selectively such that a user may choose one, or more, or even all of the major body areas to be introduced to an ultrasound treatment. The present ultrasound body suit provides for these needs.

FIELD OF THE INVENTION

The present segmented ultrasound body suit relates to ultrasound treatment devices.

SUMMARY OF THE INVENTION

The general purpose of the segmented ultrasound body suit, described subsequently in greater detail, is to provide a segmented ultrasound body suit that has many novel features that result in a segmented ultrasound body suit which is not anticipated, rendered obvious, suggested, or even implied by prior art, either alone or in combination thereof.

To accomplish this, the segmented ultrasound body suit comprises a suit assembly having an interior and an exterior spaced apart from the interior. The suit assembly has a torso and buttocks segment having an anteriorly disposed pectoral area and an abdominal area spaced apart from the pectoral area. The torso and buttocks segment has a posteriorly disposed pair of mirror image scapula areas and a pair of mirror image lumbar areas spaced apart from the scapula areas. A vertical closure is disposed posteriorly in the torso segment. The closure is provided in various areas of the torso and buttocks segment.

The suit assembly has a pair of mirror image arm segments. Each arm segment comprises a brachium and an ante brachium joined to the brachium. The suit assembly has a pair of mirror image thigh segments and a pair of mirror image calf segments.

A plurality of cutouts is disposed in the suit assembly. At least one cutout of the plurality of cutouts is disposed in each of the torso and buttocks segment, in one of each of the pair of arm segments, in one of each of the pair of thigh segments, and in one of each of the pair of calf segments. A pad is disposed within each cutout. Each of the pads is selectively produced with and without a peripheral u-channel. Each pad is selectively produced with and without a partial frustrum shape. Each contact surface varies with medical needs, whether a textured, a beaded, or a smooth contact surface. The closure varies due to production concerns.

A pocket is disposed within the u-channel. The pocket is surrounded by a substantially frustrum shape. A roof is disposed exteriorly on the pocket. A contact surface is interiorly disposed on the pad. A plurality of spaced apart beads is selectively disposed on the contact surface. A pocket is disposed between the roof and the contact surface. A floor is disposed in the pocket. The floor is proximal the contact surface. A power source is disposed within the pocket. The power source is disposed adjacent the roof. An ultrasound transducer and pressure switch is disposed within the pocket between the power source and the floor.

A chamber is disposed between the floor and the contact surface. A shaft extends from the ultrasound transducer and pressure switch to within the chamber. A disc is disposed on the shaft within the chamber. A plate is disposed within the chamber. The disc is in operational communication with the plate. An energy from the disc is transferred through the plate to the contact surface. A pressure on the roof is configured to alternately turn the ultrasound transducer and pressure switch on and off.

Thus has been broadly outlined the more important features of the present segmented ultrasound body suit so that the detailed description thereof that follows may be better understood and in order that the present contribution to the art may be better appreciated.

BRIEF DESCRIPTION OF THE DRAWINGS

Figures

DETAILED DESCRIPTION OF THE DRAWINGS

Figure 1:
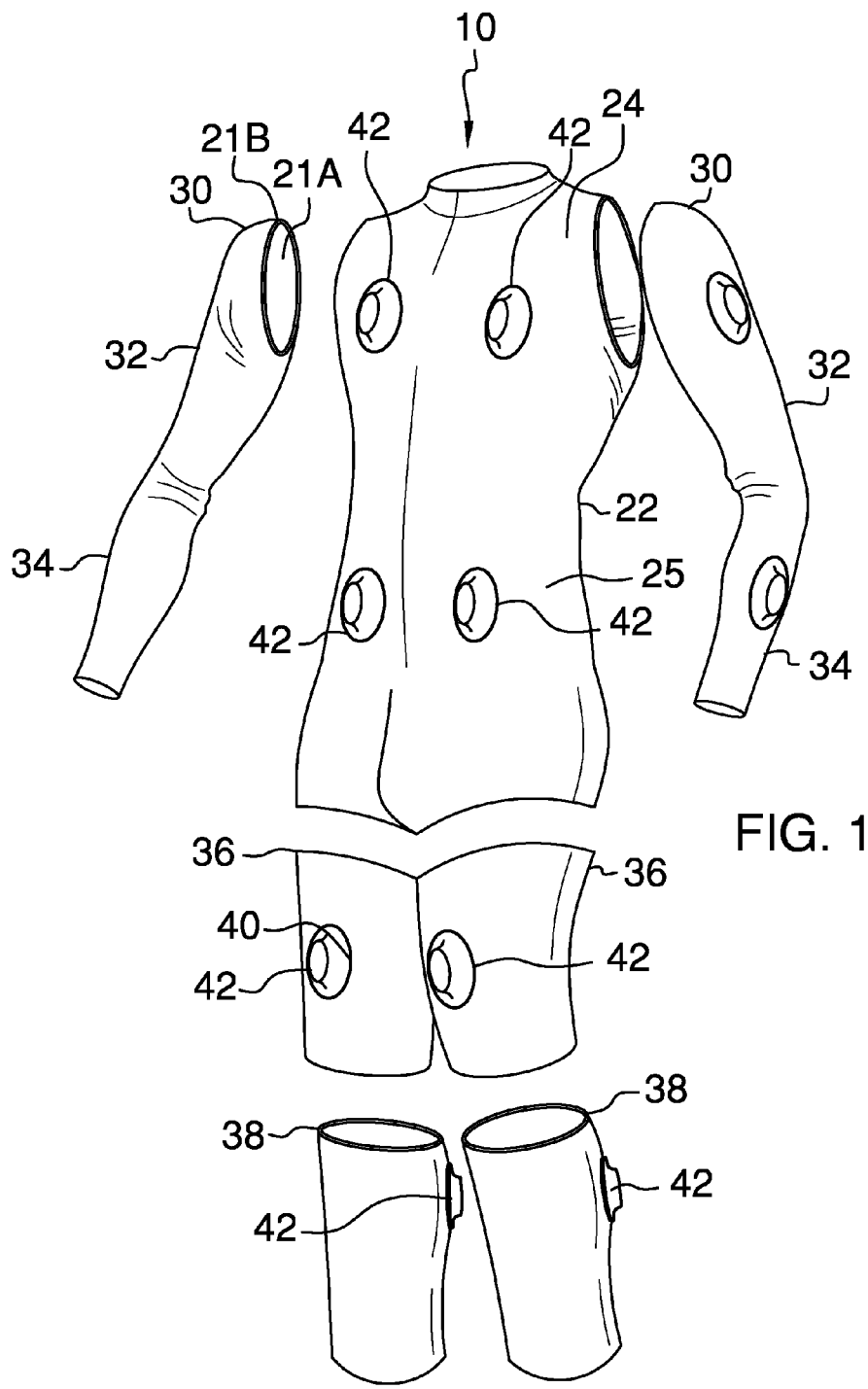
FIG. 1 is a perspective view.
Figure 2:
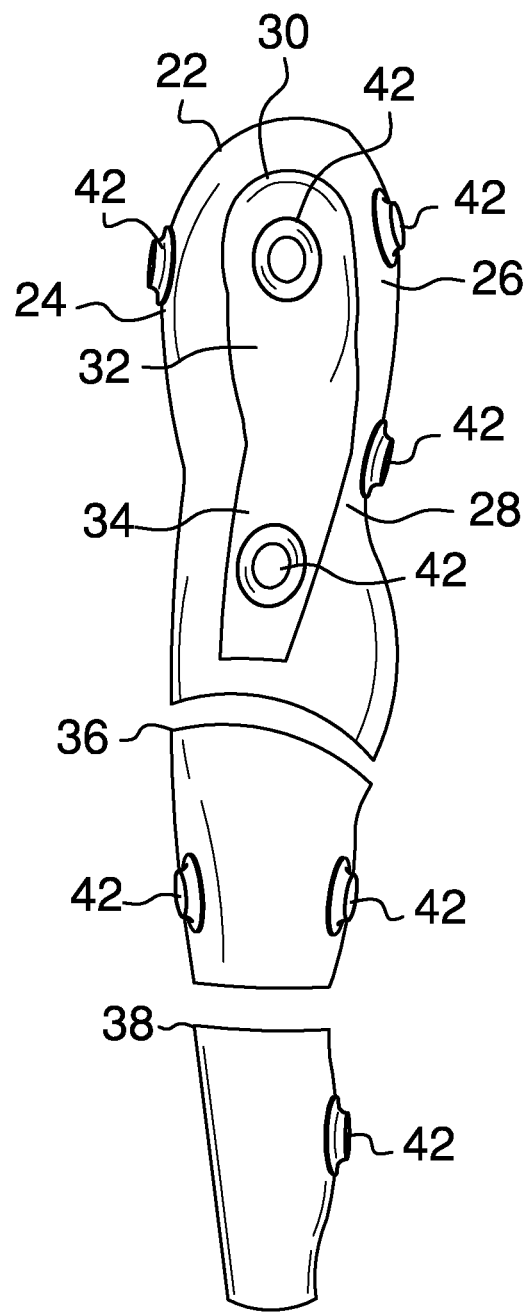
FIG. 2 is a lateral elevation view.
Figure 3:
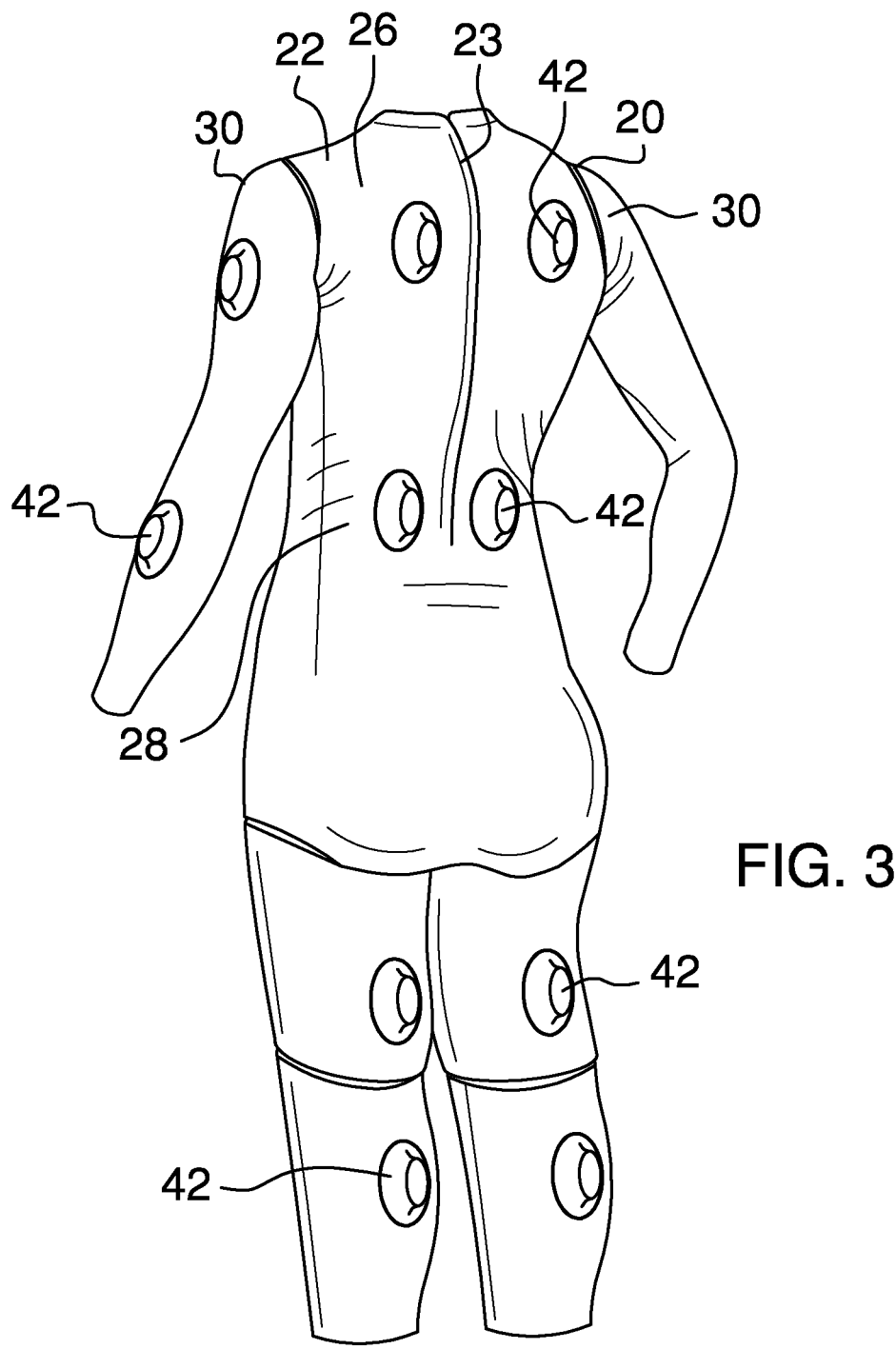
FIG. 3 is a rear perspective view.
Figure 4:
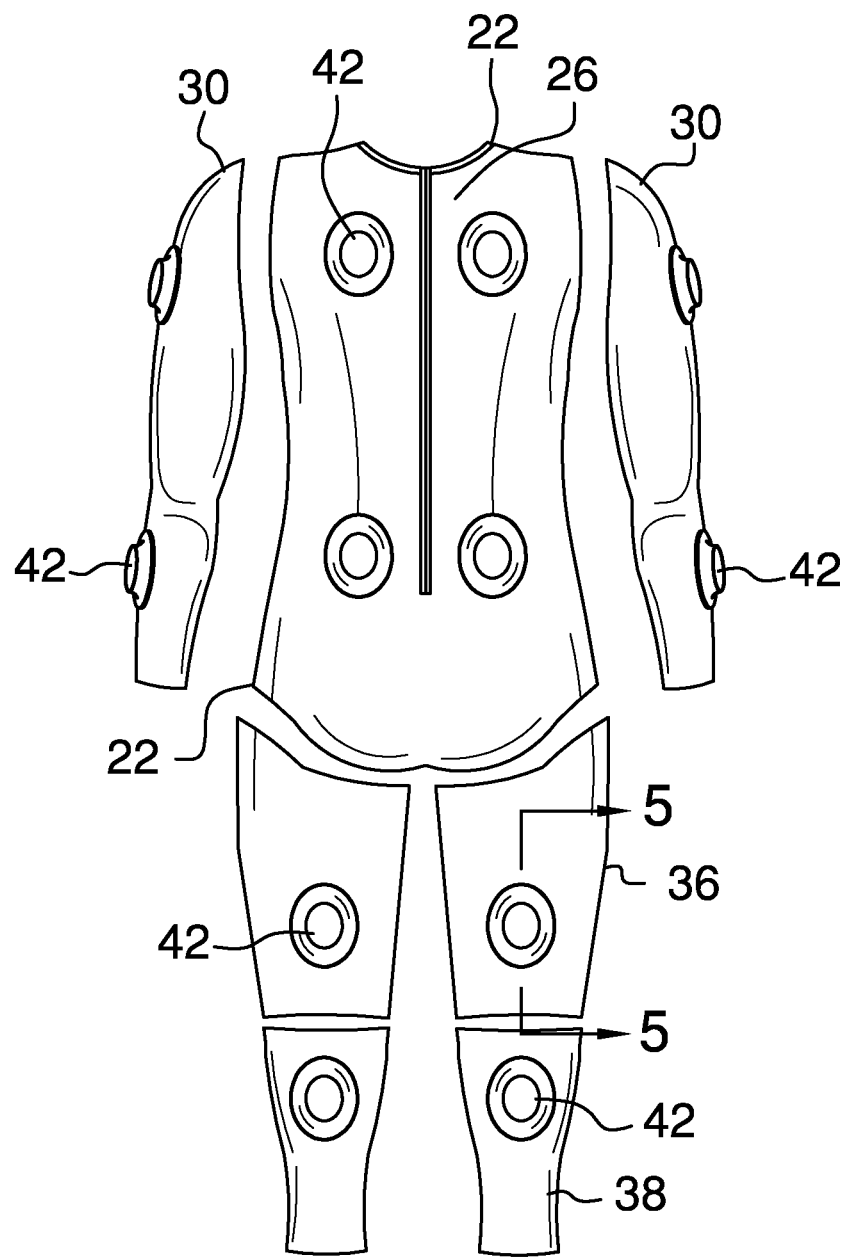
FIG. 4 is a rear elevation view.
Figure 5:
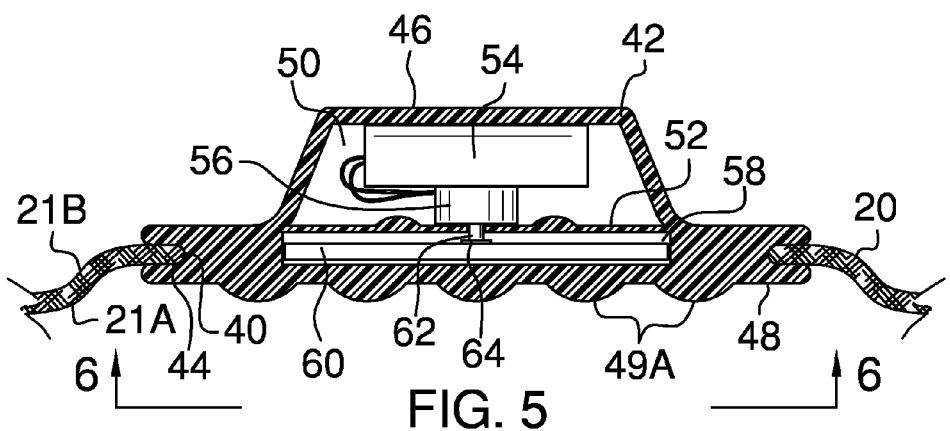
FIG. 5 is a cross sectional view of FIG. 4 taken along line 5-5.
Figure 6:
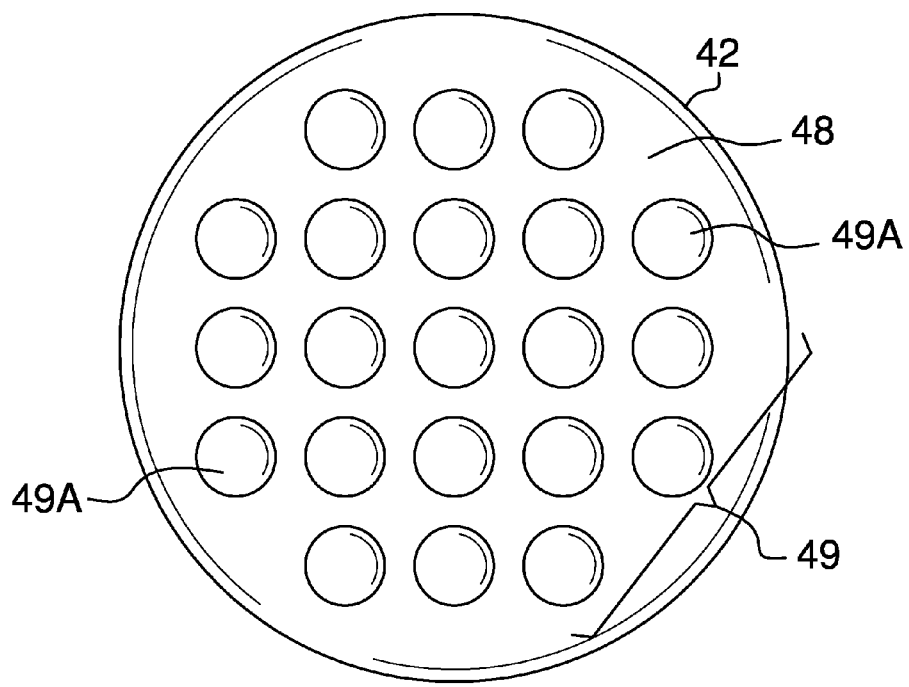
FIG. 6 is a bottom plan view of an integral pad.

With reference now to the drawings, and in particular FIGS. 1 through 6 thereof, an example of the segmented ultrasound body suit employing the principles and concepts of the present segmented ultrasound body suit and generally designated by the reference number 10 will be described.

Referring to FIGS. 1 through 6, the segmented ultrasound body suit 10 has a suit assembly 20 having an interior 21A and an exterior 21B spaced apart from the interior 21A. The suit assembly 20 has a torso and buttocks segment 22 having an anteriorly disposed pectoral area 24 and an abdominal area 25 spaced apart from the pectoral area 24. The torso and buttocks segment 22 has a posteriorly disposed pair of mirror image scapula areas 26 and a pair of mirror image lumbar areas 28 spaced apart from the scapula areas 26.

A vertical closure 23 is disposed posteriorly in the torso segment 22.

The suit assembly 20 has a pair of mirror image arm segments 30. Each arm segment 30 comprises a brachium 32 and an ante brachium 34 joined to the brachium 32. The suit assembly 20 has a pair of mirror image thigh segments 36 and a pair of mirror image calf segments 38.

A plurality of cutouts 40 is disposed in the suit assembly 20. The plurality of cutouts 40 comprises a pair of spaced apart cutouts 40 disposed in the pectoral area 24, a pair of spaced apart cutouts 40 disposed in the abdominal area 25, a pair of spaced apart cutouts 40 disposed in the scapula area 26, a pair of spaced apart cutouts 40 disposed in the lumbar area 28, a cutout 40 disposed in the brachium 32, a cutout 40 disposed in the ante brachium 34, a cutout 40 disposed anteriorly in one of each of the pair of thigh segments 36, a cutout 40 disposed posteriorly in one of each of the pair of thigh segments 36, and a cutout 40 disposed posteriorly in one of each of the pair of calf segments 38.

A plurality of pads 42 is provided. One of each of the plurality of pads 42 is disposed within each of the plurality of cutouts 40. Each pad 42 comprises a peripheral u-channel 44 affixed within each cutout 40. A pocket 50 is disposed within the u-channel 44. A roof 46 is disposed exteriorly on the pocket 50. A contact surface 48 is interiorly disposed on the pad 42. A texture 49 is disposed on the contact surface 48. The texture 49 is spaced apart beads 49A. A pocket 50 is disposed between the roof 46 and the contact surface 48. A portion of the pad 42 around the pocket 50 is frustrum shaped. A floor 52 is disposed in the pocket 50. The pad 42 is frustrum shaped around the pocket 50. The floor 52 is proximal the contact surface 48. A power source 54 is disposed within the pocket 50. The power source 54 is disposed adjacent the roof 46. An ultrasound transducer and pressure switch 56 is disposed within the pocket 50 between the power source 54 and the floor 52.

A chamber 58 is disposed between the floor 52 and the contact surface 48. A shaft 62 extends from the ultrasound transducer and pressure switch 56 to within the chamber 58. A plate 60 is disposed on the shaft 62 within the chamber 58. A disc 64 is disposed on the shaft 62 within the chamber 58. The disc 64 is in operational communication with the plate 60. The roof 46 is configured to alternately turn the ultrasound transducer and pressure switch 56 on and off with a brief pressure on the roof 46.

What is claimed is:

1. A segmented ultrasound body suit, comprising:
    a suit assembly having:
        an interior and an exterior spaced apart from the interior;
        a torso and buttocks segment having an anteriorly disposed pectoral area and an abdominal area spaced apart from the pectoral area, a posteriorly disposed pair of mirror image scapula areas and a pair of mirror image lumbar areas spaced apart from the mirror image scapula areas;
        a closure disposed in the torso segment
        a pair of mirror image arm segments, each arm segment of the pair of arm segments having a brachium and an ante brachium joined to the brachium;
        a pair of mirror image thigh segments;
        a pair of mirror image calf segments,
        a plurality of cutouts disposed in the suit assembly, at least one cutout of the plurality of cutouts disposed in the torso and buttocks segment, in one of each of the pair of arm segments, in one of each of the pair of thigh segments, in one of each of the pair of calf segments;
        a plurality of pads, one of each of the plurality of pads disposed within each cutout, each pad of the plurality of pads comprising:
            a u-channel peripherally disposed, the u-channel affixed around the suit interior and exterior at each cutout;
            a pocket disposed within the peripheral u-channel;
            a roof disposed exteriorly on the pocket;
            a contact surface disposed interiorly on the pad;
            a pocket disposed between the roof and the contact surface;
            a floor disposed in the pocket, the floor proximal the contact surface;
            a power source disposed within the pocket, the power source adjacent the roof;
            an ultrasound transducer and pressure switch disposed within the pocket between the power source and the floor;
            a chamber disposed between the floor and the contact surface;
            a plate disposed within the chamber;
            a shaft extended from the ultrasound transducer and pressure switch to within the chamber; and
            a disc disposed on the shaft within the chamber, the disc in operational communication with the plate;
        wherein the roof is configured to alternately turn the ultrasound transducer and pressure switch on and off with a brief pressure on the roof.

2. The segmented ultrasound body suit of claim 1 wherein the pad around the pocket is frustrum shaped.

3. The segmented ultrasound body suit of claim 1 wherein the contact surface comprises a texture.

4. The segmented ultrasound body suit of claim 2 wherein the contact surface comprises a texture.

5. The segmented ultrasound body suit of claim 3 wherein the texture comprises a plurality of spaced apart beads.

6. The segmented ultrasound body suit of claim 4 wherein the texture comprises a plurality of spaced apart beads.

7. A segmented ultrasound body suit, comprising:
    a suit assembly having:
        an interior and an exterior spaced apart from the interior;
        a torso and buttocks segment having an anteriorly disposed pectoral area and an abdominal area spaced apart from the pectoral area, a posteriorly disposed pair of mirror image scapula areas and a pair of mirror image lumbar areas spaced apart from the mirror image scapula areas;
        a closure disposed in the torso segment
        a pair of mirror image arm segments, each arm segment of the pair of arm segments having a brachium and an ante brachium joined to the brachium;
        a pair of mirror image thigh segments;
        a pair of mirror image calf segments,
        a plurality of cutouts disposed in the suit assembly, at least one cutout of the plurality of cutouts disposed in the torso and buttocks segment and in one of each of the pair of arm segments and in one of each of the pair of thigh segments and in one of each of the pair of calf segments;
        a plurality of pads, one of each of the plurality of pads disposed within each cutout, each pad of the plurality of pads comprising:
            a u-channel peripherally disposed, the u-channel affixed around the suit interior and exterior at each cutout;
            a pocket disposed within the peripheral u-channel;
            a roof disposed exteriorly on the pocket;
            a contact surface disposed interiorly on the pad;
            a plurality of spaced apart beads disposed on the contact surface;
            a pocket disposed between the roof and the contact surface;
            a floor disposed in the pocket, the floor proximal the contact surface;
            a power source disposed within the pocket, the power source adjacent the roof;
            an ultrasound transducer and pressure switch disposed within the pocket between the power source and the floor;
            a chamber disposed between the floor and the contact surface;
            a plate disposed within the chamber;
            a shaft extended from the ultrasound transducer and pressure switch to within the chamber; and
            a disc disposed on the shaft within the chamber, the disc in operational communication with the plate;
        wherein the roof is configured to alternately turn the ultrasound transducer and pressure switch on and off with a brief pressure on the roof.

8. The segmented ultrasound body suit of claim 7 wherein the pad has a partial frustrum shape.

9. The segmented ultrasound body suit of claim 7 wherein the contact surface comprises a texture.

10. The segmented ultrasound body suit of claim 8 wherein the contact surface comprises a texture.

11. The segmented ultrasound body suit of claim 9 wherein the texture comprises a plurality of spaced apart beads.

12. The segmented ultrasound body suit of claim 10 wherein the texture comprises a plurality of spaced apart beads.

13. A segmented ultrasound body suit, comprising:
a suit assembly having:
an interior and an exterior spaced apart from the interior;
a torso and buttocks segment having an anteriorly disposed pectoral area and an abdominal area spaced apart from the pectoral area, a posteriorly disposed pair of mirror image scapula areas and a pair of mirror image lumbar areas spaced apart from the mirror image scapula areas;
a vertical closure disposed posteriorly in the torso segment
a pair of mirror image arm segments, each arm segment of the pair of arm segments having a brachium and an ante brachium joined to the brachium;
a pair of mirror image thigh segments;
a pair of mirror image calf segments,
a plurality of cutouts disposed in the suit assembly, each cutout of the plurality of cutouts comprising:
a pair of spaced apart cutouts disposed in the pectoral area, a pair of spaced apart cutouts disposed in the abdominal area, a pair of spaced apart cutouts disposed in the scapula area, a pair of spaced apart cutouts disposed in the lumbar area, a cutout disposed in the brachium, a cutout disposed in the ante brachium, a cutout disposed anteriorly in one of each of the pair of thigh segments, a cutout disposed posteriorly in one of each of the pair of thigh segments, a cutout disposed posteriorly in one of each of the pair of calf segments;
a plurality of partially frustrum shaped pads, one of each of the plurality of pads disposed within each cutout of the plurality of cutouts, each pad comprising:
a u-channel peripherally disposed on the pad, the u-channel affixed around the suit interior and exterior at each cutout;
a pocket disposed within the peripheral u-channel;
a roof disposed exteriorly on the pocket;
a contact surface disposed interiorly on the pad;
a texture disposed on the contact surface;
a pocket disposed between the roof and the contact surface;
a floor disposed in the pocket, the floor proximal the contact surface;
a power source disposed within the pocket, the power source adjacent the roof;
an ultrasound transducer and pressure switch disposed within the pocket between the power source and the floor;
a chamber disposed between the floor and the contact surface;
a plate disposed within the chamber;
a shaft extended from the ultrasound transducer and pressure switch to within the chamber; and
a disc disposed on the shaft within the chamber, the disc in operational communication with the plate;
wherein the roof is configured to alternately turn the ultrasound transducer and pressure switch on and off with a brief pressure on the roof.

14. The segmented ultrasound body suit of claim 13 wherein the texture comprises a plurality of spaced apart beads.

15. The segmented ultrasound body suit of claim 13 wherein the suit assembly is at least partially comprised of carbon fiber.

16. The segmented ultrasound body suit of claim 14 wherein the suit assembly is at least partially comprised of carbon fiber.

* * * * *